US011235172B2

(12) United States Patent
Thornton

(10) Patent No.: US 11,235,172 B2
(45) Date of Patent: Feb. 1, 2022

(54) RADIATION TREATMENT PLANNING REAL-TIME USER INTERFACE

(71) Applicant: Varian Medical Systems, Inc., Palo Alto, CA (US)

(72) Inventor: Kenneth B. Thornton, Charlottesville, VA (US)

(73) Assignee: Varian Medical Systems, Inc., Palo Alto, CA (US)

(*) Notice: Subject to any disclaimer, the term of this patent is extended or adjusted under 35 U.S.C. 154(b) by 108 days.

(21) Appl. No.: 16/713,548

(22) Filed: Dec. 13, 2019

(65) Prior Publication Data

US 2021/0178187 A1 Jun. 17, 2021

(51) Int. Cl.
*A61N 5/10* (2006.01)

(52) U.S. Cl.
CPC ......... *A61N 5/1031* (2013.01); *A61N 5/1067* (2013.01); *A61N 2005/1074* (2013.01)

(58) Field of Classification Search
CPC ............... A61N 5/1031; A61N 5/1067; A61N 2005/1074
See application file for complete search history.

(56) References Cited

U.S. PATENT DOCUMENTS

| 8,604,450 B2 | 12/2013 | Mohr | |
|---|---|---|---|
| 2005/0111621 A1* | 5/2005 | Riker | G16H 70/20 378/65 |
| 2016/0129282 A1* | 5/2016 | Yin | G16H 20/40 600/1 |
| 2017/0072221 A1 | 3/2017 | Nord | |

* cited by examiner

*Primary Examiner* — Michael C Bryant
(74) *Attorney, Agent, or Firm* — Fitch, Even, Tabin & Flannery LLP

(57) ABSTRACT

A control circuit carries out various actions to facilitate speedy user interaction involving adjustments to radiation dosing that corresponds to a particular mixed radiation treatment plan. These actions can include remixing particular multi-criteria optimization radiation treatment plans.

20 Claims, 5 Drawing Sheets

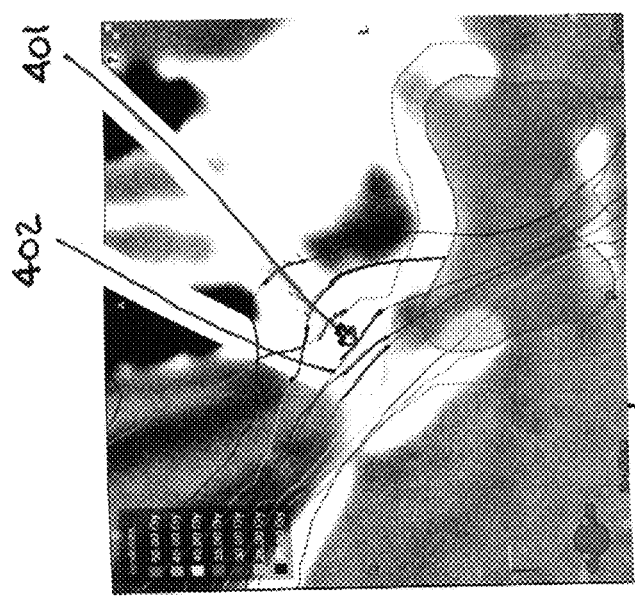
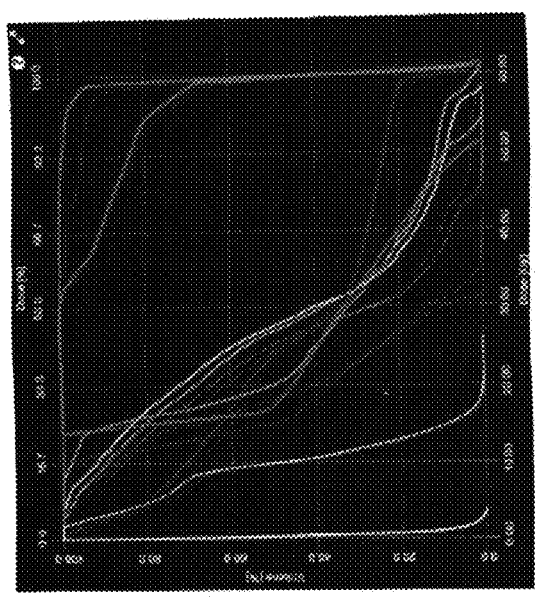
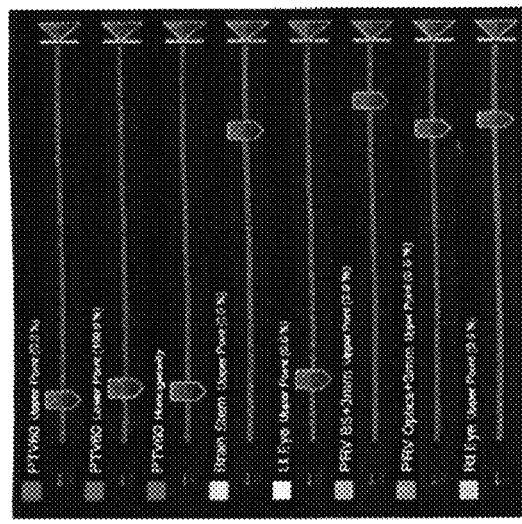
FIG. 5

RADIATION TREATMENT PLANNING REAL-TIME USER INTERFACE

TECHNICAL FIELD

These teachings relate generally to radiation treatment plans and more particularly to user interfaces that facilitate developing and/or modifying a radiation treatment plan.

BACKGROUND

The use of radiation to treat medical conditions comprises a known area of prior art endeavor. For example, radiation therapy comprises an important component of many treatment plans for reducing or eliminating unwanted tumors. Brachytherapy is one form of radiotherapy where one or more sealed radiation sources are physically placed inside or next to a patient's target treatment volume. By another approach therapeutic radiation is administered via an external beam.

Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume. A so-called treatment plan often serves in the foregoing regards.

Such treatment plans are often optimized prior to use. It will be understood that the expression "optimize," "optimized," and "optimizing" as used herein should not be confused with the idea of identifying an objectively "optimum" plan that is superior to all other possible plans. Instead, such optimization comprises iteratively assessing alternatives to a given plan to attempt to identify a better plan. This can comprise, for example, trying and evaluating iterative alterations to each (or many) of the operating parameters that characterize a particular treatment method and platform.

In some cases the planning process will accommodate permitting a user to modify some parameter of interest. As one example in these regards, a user may be presented with a plurality of isodose contours that correspond to a particular radiation treatment plan of interest, and the user may be allowed to, for example, click and drag some part of a given contour. Unfortunately, the calculations that underlie a typical planning process can be computationally intense. As a result, there may be a considerable lag in time before the user can see and thereby comprehend the overall effect of such a modification.

BRIEF DESCRIPTION OF THE DRAWINGS

The above needs are at least partially met through provision of the radiation treatment planning real-time user interface apparatus and method described in the following detailed description, particularly when studied in conjunction with the drawings, wherein:

FIG. 5 comprises a screen shot as configured in accordance with various embodiments of these teachings.

Figure 1:
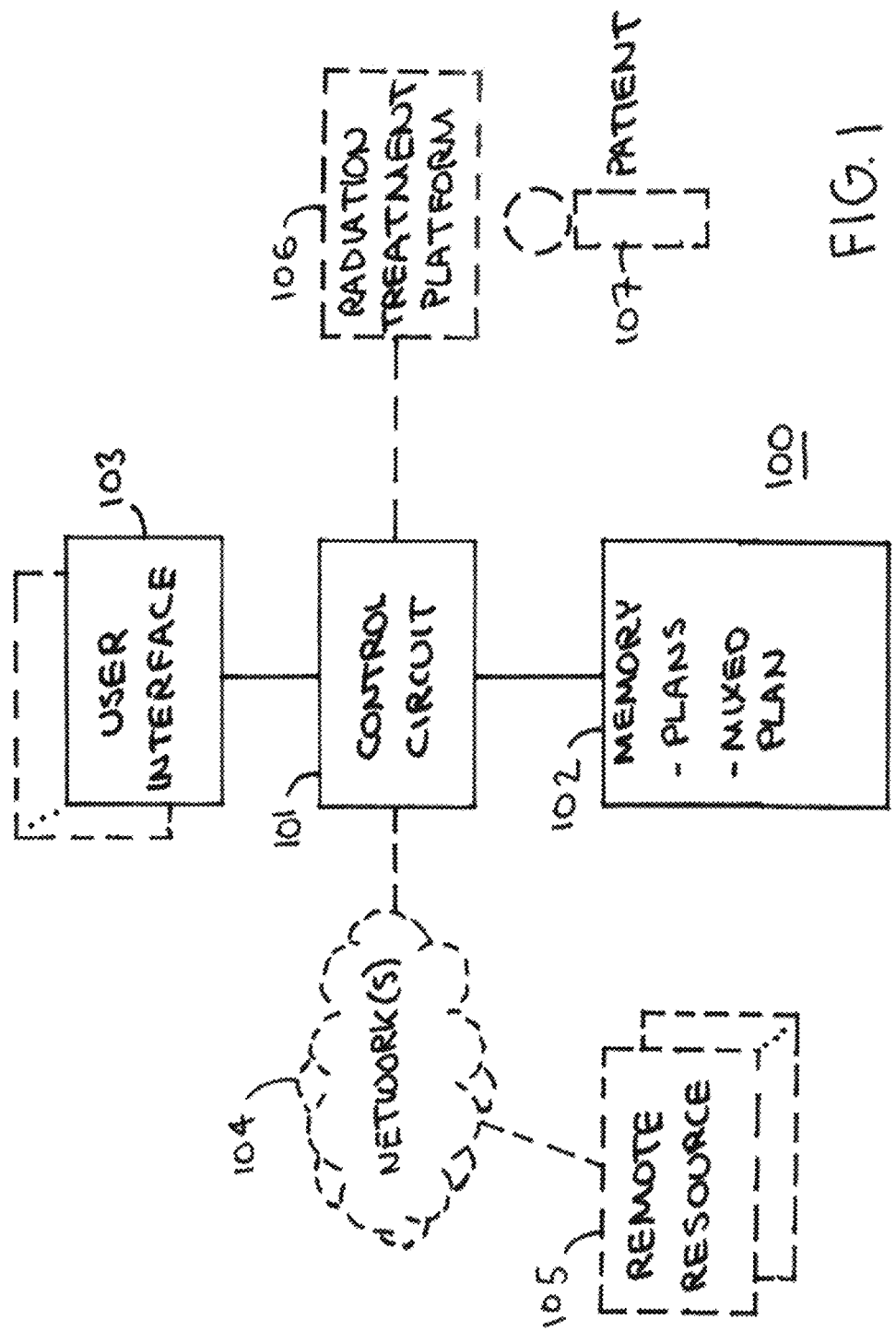
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, pursuant to these various embodiments a control circuit carries out various actions to facilitate speedy user interaction involving adjustments to radiation dosing that corresponds to a particular mixed radiation treatment plan.

By one approach the control circuit accesses a plurality of different radiation treatment plans for a particular patient and forms a mixed radiation treatment plan from that plurality of different radiation treatment plans. The control circuit then presents on a display a plurality of dose volume histograms for the mixed radiation treatment plan. In a typical application setting, at least one of the dose volume histograms depicts a first histogram that relates radiation dose to a target volume and another of the dose volume histograms depicts a second histogram that relates radiation dose to an organ at risk. These teachings will also accommodate also presenting on the display an overlay of calculated radiation dose from the mixed radiation treatment plan on a treatment planning image volume. The latter can comprise, for example, displaying at least one of a set of isodose contours or dose color washes.

Upon detecting a user's manipulation of one of the aforementioned dose volume histograms, the control circuit can respond by modifying, on the display, at least one other of the dose volume histograms as a function of a mix of at least two of the plurality of different radiation treatment plans. In addition, upon detecting a user's real-time manipulation of the overlay of the calculated radiation dose, the control circuit can respond by modifying, on the display and in real-time, both the plurality of dose volume histograms and the overlay of the calculated radiation dose.

By one approach, the control circuit modifies the display of the aforementioned other dose volume histogram (or histograms) as a function of a mix of at least two of the plurality of different radiation treatment plans by varying a weighting factor as corresponds to a representative multi-dimensional vector for mixed radiation treatment plans.

These teachings will also accommodate the control circuit also presenting on the display, simultaneously with presenting the plurality of dose volume histograms, a plurality of user-interactive indicators that collectively represent dosing trade-offs amongst a plurality of patient volumes. In such a case, these teachings will accommodate modifying the display of the dose volume histograms in response to a user's manipulation of one of the plurality of user-interactive indicators.

These teachings are highly flexible and practical in practice. These teachings can be utilized, for example, both when looking to administer radiation via brachytherapy or via an external radiation beam.

These and other benefits may become clearer upon making a thorough review and study of the following detailed description. Referring now to the drawings, and in particular to FIG. 1, an illustrative enabling apparatus 100 that is compatible with many of these teachings will now be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

In this example the control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to radiation treatment plans as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

The control circuit 101 operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user. For the sake of an illustrative example, the following description presumes that the user interface 103 at least includes one display and at least one cursor-control device.

If desired, the control circuit 101 can optionally couple to one or more data/communication networks 104. So configured the control circuit 101 can communicate with other elements including one or more remote resources 105. These remote resources 105 may provide the control circuit 101 with data pertaining to a particular patient, or other information regarding, for example, specific radiation treatment platforms. Networks, including both wireless and non-wireless networks, are well understood in the art and require no particular elaboration here.

Also if desired, the control circuit 101 can optionally couple to a radiation treatment platform 106. Generally speaking, a radiation treatment platform 106 serves to deliver therapeutic radiation to a corresponding particular patient 107. These teachings are generally applicable for use with any of a wide variety of radiation treatment platforms and/or application settings including brachytherapy and various external beam therapies. As one illustrative example, in a typical external beam therapy application setting the radiation treatment platform 106 will include an x-ray source that emits a beam of radiation. The x-ray source can comprise, for example, a radio-frequency (RF) linear particle accelerator-based (linac-based) x-ray source, such as the Varian Linatron M9. The linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) and high energy electrons. A typical radiation treatment platform 106 may also include one or more support surfaces (such as a couch) to support the patient 107 during the treatment session, a gantry or other mechanism to permit selective movement of the x-ray source, and one or more components (such as jaws, multi-leaf collimators, and so forth) to provide selective beam shaping and/or beam modulation as desired.

Figure 2:
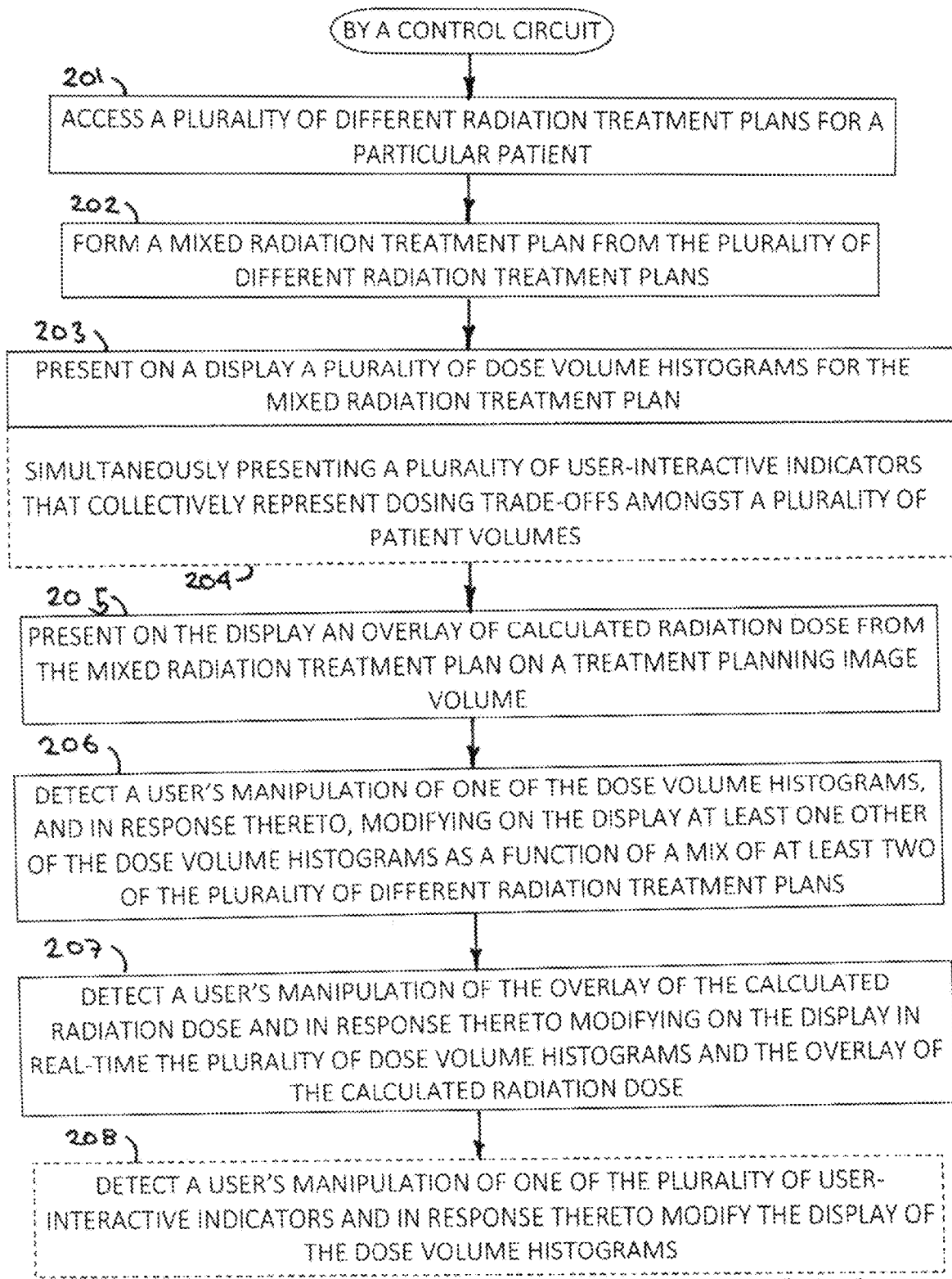
FIG. 2 comprises a flow diagram as configured in accordance with various embodiments of these teachings.

Referring now to FIG. 2, a process 200 that can be carried out by the above-described control circuit 101 will now be presented. In particular, this process 200 serves to facilitate shaping a radiation treatment dose.

At block 201 the control circuit 101 accesses a plurality of different radiation treatment plans for a particular patient 107. By one approach, and as an illustrative example, some or all of those different radiation treatment plans are available to the control circuit 101 from the aforementioned memory 102. As noted, these radiation treatment plans, although different from one another, are all for a particular patient 107 and are not more generally conceived in those regards.

These teachings are highly flexible in practice and will accommodate different treatment paradigms. For example, by one approach, the aforementioned plurality of different radiation treatment plans all presume the administration of radiation to the particular patient 107 via brachytherapy. By another approach, the aforementioned plurality of different radiation treatment plans all presume the administration of radiation to the particular patient via an external radiation beam.

In this example, each of the plurality of different radiation treatment plans comprises a multi-criteria optimization radiation treatment plan. As used herein, the foregoing expression will be understood to refer to radiation treatment plans that were optimized using multi-criteria optimization. Multi-criteria optimization is known in the art. See, for example, US patent application publication number 2017/0072221 (entitled KNOWLEDGE BASED MULTI-CRITERIA OPTIMIZATION FOR RADIOTHERAPY TREATMENT PLANNING), the contents of which are fully incorporated herein by this reference.

As will be elaborated upon in more detail below, by one approach each of these multi-criteria optimization radiation treatment plans includes (i.e., is represented by) a representative multi-dimensional vector (denoted, for example, by $x_i$).

The number of different radiation treatment plans for the particular patient 107 that are so accessed by the control circuit 101 can vary as desired. There may be, for example, 50 or more such plans, 100 or more such plans, 500 or more such plans, 1000 or more such plans, and so forth as desired.

At block 202, this process 200 then provides for having the control circuit form a so-called mixed radiation treatment plan from the aforementioned plurality of different radiation treatment plans. An illustrative example in these regards will be provided further herein.

Figure 3:
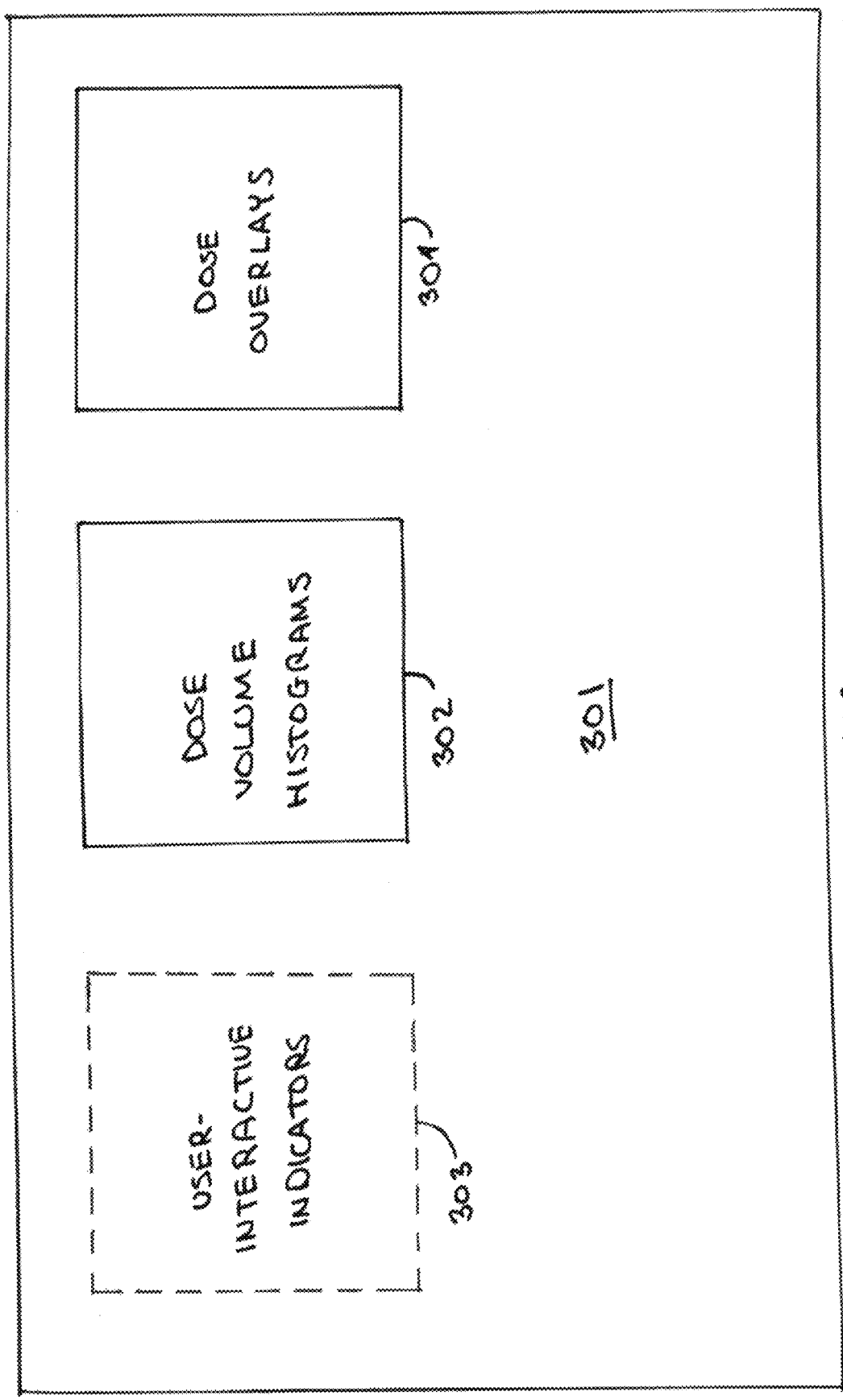
FIG. 3 comprises a schematic screen shot as configured in accordance with various embodiments of these teachings.

At block 203, and referring as well to FIG. 3, the control circuit 101 presents on a display 301 that comprises a part of the aforementioned user interface 103 a plurality of dose volume histograms 302 for the aforementioned mixed radiation treatment plan.

Dose volume histograms are well understood in this part. Dose volume histograms (DVH's) typically represent three-dimensional dose distributions in a graphical two-dimensional format (the three-dimensional dose distributions being created, for example, in a computerized radiation-treatment planning system based on a three-dimensional reconstruction of an X-ray computed tomography scan and study). The "volume" referred to a DVH analysis can be, for example, the radiation-treatment target, a healthy organ located near such a target, an arbitrary structure, and so forth.

DVH's are often visualized in either of two ways: as differential DVH's or as cumulative DVH's. With differential DVH's column height for a given dose bin corresponds to the volume of the structure that receives that dose. Bin doses typically extend along the horizontal axis while structure volumes (either percent or absolute volumes) extend along the vertical axis.

A cumulative DVH is typically plotted with bin doses along the horizontal axis but has a column height for the first bin that represents the volume of structure(s) that receive greater than or equal to that dose. The column height of the second bin then represents the volume of structure(s) that receive greater than or equal to that dose, and so forth. With high granularity a cumulative DVH often appears as a smooth line graph. For many application settings cumulative DVH's are preferred over differential DVH's but the present process 200 can accommodate either approach.

In a typical application setting, at least one of the presented dose volume histograms depicts a first histogram that relates radiation dose to a target volume in the particular patient 107 (such as, for example, a tumor) while another of the dose volume histograms depicts a second histogram that relates radiation dose to a first organ at risk (typically an organ that is either proximal to the target volume or otherwise in-line/exposed to radiation during at least some part of the radiation treatment). In many cases this presentation will include a DVH for each of a plurality of such organs at risk. These teachings will accommodate presenting these various DVH's in a differentiated manner (for example, by using differently colored lines, lines of different thickness or type, and so forth). Presenting DVHs comprises a well-understood area of prior art endeavor and therefore further elaboration in these regards is not provided here for the sake of brevity.

With continued reference to both FIGS. 2 and 3, if desired, these teachings will optionally support (at block 204) also presenting on the display 301 a plurality of user-interactive indicators 303 that collectively represent dosing trade-offs amongst a plurality of patient volumes (including both target volumes and organs at risk). By one approach these user-interactive indicators are presented on the display 301 simultaneously with presenting the aforementioned plurality of dose volume histograms. These user-interactive indicators can all share a same form factor and appearance or can be different from one another if desired. These teachings will accommodate using any of a variety of user-interactive indicator form factors, including but not limited to sliders, rotating knobs, touch bars, a row of discrete buttons/lights, and so forth.

These teachings will accommodate a variety of dosing trade-offs that can be represented via these user-interactive indicators 303. As regards the patient's target volume, examples can include one or more specific point locations therein (such as, relatively speaking, and upper point, a lower point, or a central point) as well as a parameter that represents general dosing homogeneity as regards the target volume. As regards organs at risk, these teachings will accommodate presenting a user-interactive indicator for each of a variety of relevant organs at risk. As one illustrative example in these regards, this might include presenting a user-interactive indicator for each of the patient's left eye, right eye, optic nerve, brainstem, and so forth.

In any event, at block 205 this process 200 provides for presenting on the display 301 an overlay of calculated radiation dose from the mixed radiation treatment plan on a treatment planning image volume (or volumes) as denoted in FIG. 3 by reference numeral 304. By one approach these calculated radiation doses are presented as isodose lines that are overlaid on, for example, a two-dimensional presentation drawn from one or more CT slices or images. In such a case, each isodose lines can represent a particular dosing level (expressed, for example, as a particular number or range using Gray units). By one approach such lines can be visually distinguished from one another by using a different color for each such line value or range.

At block 206 the control circuit 101 detects a user's manipulation of one of the aforementioned dose volume histograms 302. In response, the control circuit 101 modifies on the display 301 at least one other of the dose volume histograms. While such a response in general can be found in the prior art, per these teachings and contrary to such prior art approaches this modification occurs as a function of a mix of at least two of the plurality of the aforementioned different radiation treatment plans. A more specific description will be presented below in these regards.

Generally speaking, by one approach, such mixing can rely upon differently weighting the different radiation treatment plans that are so mixed together. By using this approach, the described response can occur in real time. (As used herein, "real time" will be understood to mean a range of times from instantaneously to 0.2 seconds.) Being able to respond so quickly can greatly improve the user experience, can contribute to a more intuitive understanding of how such a manipulation has a corresponding effect upon overall dosing, and can also lead to reduced overall time to facilitate shaping a radiation treatment dose prior to administering that treatment to the particular patient 107.

Somewhat similarly, and referring now to block 207, the control circuit 101 can also be configured to detect the user's manipulation of the above-described overlay 304 of the calculated radiation dose and to respond to such manipulation by modifying on the display 301 in real time the plurality of dose volume histograms as well as the other isodose lines presented on the overlay of the calculated radiation dose. Not only does this permit the user to understand the impact of a particular manipulation to the overlaid dose lines by visually presenting those results in the dose overlay context, the user can also essentially immediately see and intuitively understand the consequence of such a manipulation when viewed using the dose volume histogram paradigm.

If desired, and referring to optional block 208, these teachings will also accommodate having the control circuit 101 detect a user's manipulation of one of the plurality of above-described user-interactive indicators and in response thereto to modify the display of the dose volume histograms 302 (in addition to also, for example, modifying untouched user-interactive indicators as appropriate).

Figure 4:
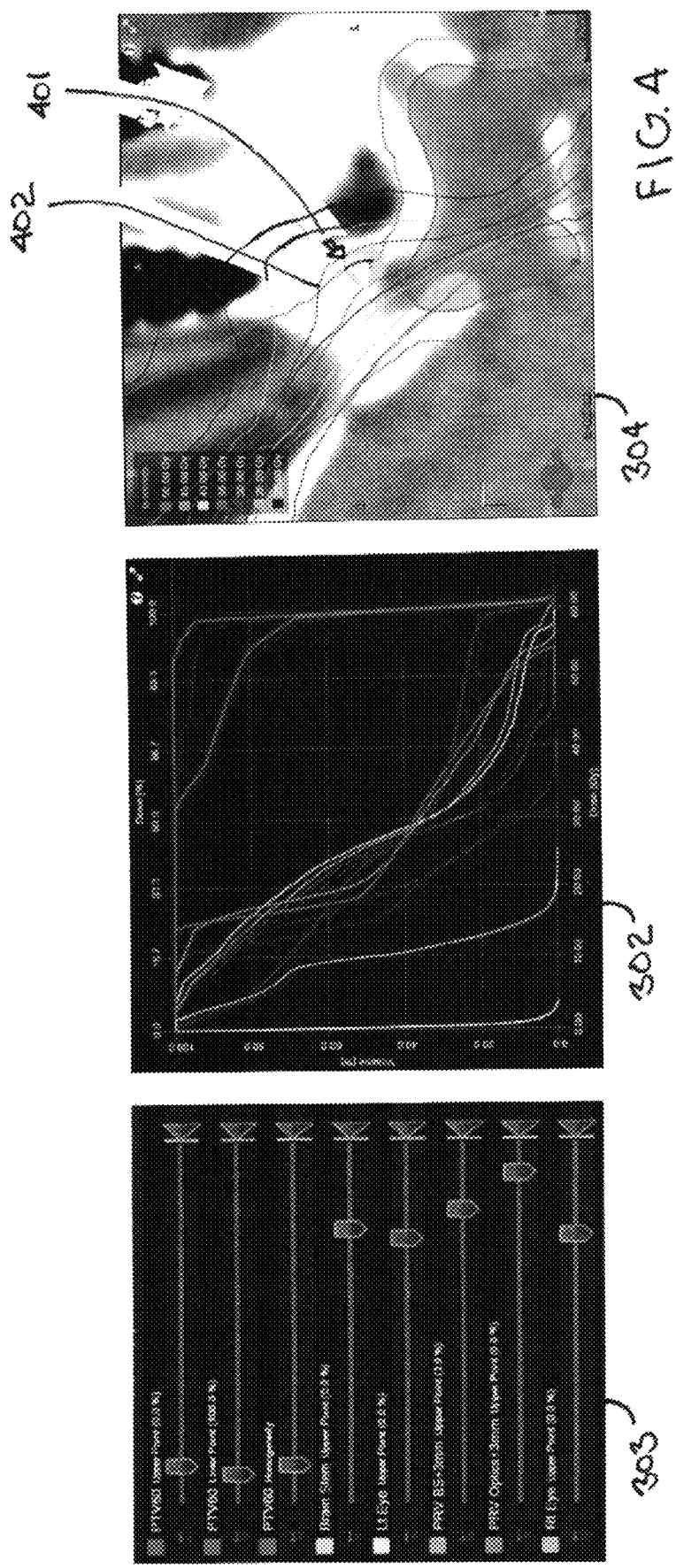
FIG. 4 comprises a screen shot as configured in accordance with various embodiments of these teachings.

Referring now to FIGS. 4 and 5, a particular specific example will be provided. It should be understood that the specific details of this example are intended to serve an illustrative purpose and should not be considered limiting in any way.

In FIG. 4, the user-interactive indicators 303, dose volume histograms 302, and dose overlays 304 all currently represent a mixed radiation treatment plan in accord with blocks 203, 204, and 205 of FIG. 2. In the dose overlay 304 region the user manipulates a cursor 401 to identify a particular point on a particular isodose line 402. The user then clicks on the cursor 401 at that point to select and grab that particular point on that isodose line 402. Having selected that point, the user then moves the cursor 401 to drag that isodose line 402 to a new position as shown in FIG. 5. As this occurs, and in real time, the control circuit 101 mixes two or more of the available different radiation treatment plans to calculate the corresponding effect of that movement upon the dosing of other volumes. Those calculations can be performed very rapidly as compared to other approaches that have traditionally be employed to attempt to provide a similar user experience (all other things being equal, such as use of a same computing platform). These recalculations are then utilized by the control circuit 101 to adjust corresponding isodose lines in the dose overlay 304 region as shown in FIG. 5 and also to adjust corresponding dose volume histograms in that region 302 of the display 301.

Further elaboration regarding the above-mentioned mixing of different radiation treatment plans will now be presented. Again, it will be understood that the specifics of this discussion are intended to serve an illustrative purpose and are not intended to necessarily suggest any specific limitations in these regards.

The present state of the art in multi-criteria-optimization (MCO) for radiation treatment planning is for the planning system to calculate a plurality of treatment plans and then allow the user in real-time to mix the plans in order to achieve one or more dosimetric quality objectives (DQOs) with respect to one or more planning structures of interest (such as target volume's or organs-at-risk (OAR)).

For the sake of an illustrative example it is presumed here that there are P treatment plans available in the aforementioned memory 102. Each plan $x_i$ (i=1, ..., P) is a vector of M parameters used to deliver the plan (e.g., beamlet weights for external beam plans or dwell-times for brachytherapy plans). Each plan $x_i$ has information needed to calculate radiation dose to a planning treatment volume (PTV). From the calculated dose for plan $x_i$, a vector $q_i$ of N DQOs can be calculated. Each element of the vector $q_i$ corresponds to a DQO of one of the structures of interest. Without loss of generality, one can assume that higher values of a DQO are better (i.e., higher quality).

The entire set of P treatment plans be can represented as a matrix $X=(x_1 \ldots x_P)$ having dimension M×P. From the matrix X, the entire set of P DQOs can be calculated and represented as a matrix $Q=(q_1 \ldots q_P)$ having dimension N×P. The planning system allows the user to "mix" plans to explore dosimetric trade-offs.

Example

Assume there are P=2 treatment plans $x_1$ and $x_2$. Let there be N=2 DQOs. Plan 1 has DQO vector $$q_1 = \begin{pmatrix} 95 \\ 65 \end{pmatrix}$$

and plan 2 has DQO vector $$q_2 = \begin{pmatrix} 85 \\ 75 \end{pmatrix}.$$

Assume that the $1^{st}$ element of each vector corresponds to a target DQO and the $2^{nd}$ element of each vector corresponds to an OAR DQO.

For the sake of this example it is assumed that the planner is not willing to deliver either plan to the patient, but rather wants to mix the plans to achieve a specific set of DQOs. If the planner wishes to increase the quality objective of the OAR at the expense of reducing the quality objective to the target, she may just average the two plans. The result is referred to as and understood to be a mixed plan $x^{mix}$ with DQO vector $q^{mix}$.

$$x^{mix} = 0.5 \times x_1 + 0.5 \times x_2$$

$$q^{mix} = \begin{pmatrix} q_{Target} \\ q_{OAR} \end{pmatrix} = 0.5 \times \begin{pmatrix} 95 \\ 65 \end{pmatrix} + 0.5 \times \begin{pmatrix} 85 \\ 75 \end{pmatrix} = \begin{pmatrix} 90 \\ 70 \end{pmatrix}$$

It is also convenient to allow the user to set a minimum limit value for each quality parameter. This can be represented by a vector $q^{limit}$ also of length N. In the above example, the planner could set $q_{Target}^{limit}=92$ if she has a requirement that the target DQO must remain ≥92. With this limit in place, the mixed plan above would not be acceptable, but the mixed plan below would be:

$$x^{mix}=0.7 \times x_1 + 0.3 \times x_2$$

$$q^{mix} = 0.7 \times \begin{pmatrix} 95 \\ 65 \end{pmatrix} + 0.3 \times \begin{pmatrix} 85 \\ 75 \end{pmatrix} = \begin{pmatrix} 92 \\ 68 \end{pmatrix}$$

In the equation above, $$\alpha = \begin{pmatrix} 0.7 \\ 0.3 \end{pmatrix}$$

is the mixing vector since $x^{mix}$ and $q^{mix}$ were formed by taking 70% of plan 1 and 30% of plan 2.

The elements of $\alpha$ are non-negative and must sum to 1. In the general case, $\alpha$ will have length P (equal to the number of plans in the plan database). The mixed plan will be $x^{mix}=X \times \alpha$ and the mixed DQO vector will be $q^{mix}=Q \times \alpha$. It will be convenient to also refer to element i of the mixed DQO vector $q^{mix}$ as $(Q \times \alpha)_i$.

In a typical embodiment, each of the N DQOs can be associated with a slider on a graphical user interface as described above. In one convention, moving a slider i left results in a higher/better value $q_i^{mix}$ for its associated DQO and moving a slider i to the right results in a lower/worse value $q_i^{mix}$ for its associated DQO. It is apparent that the absolute left-most and right-most values $q_i^{left}$ and $q_i^{right}$ must correspond to the maximum and minimum values of row i of matrix Q, respectively. The position of slider i will correspond to $q_i^{mix}=(Q \times \alpha)_i$ which must be $\geq q_i^{limit}$.

Limiting the position of slider i may restrict the ranges that all other sliders can move. (Each restriction limits the possible a values which in turn limits the range that $(Q \times \alpha)_i$ can take). The restricted left and right ranges of all sliders are represented by the vectors $q^{max}$ and $q^{min}$.

In summary, by one approach there are 6 quantities associated with each slider:
- $q_i^{left}$ and $q_i^{right}$ are the absolute ranges of slider i (the maximum and minimum of row i of Q)
- $q_i^{limit}$ is the limit position of slider i
- $q_i^{max}$ and $q_i^{min}$ are the restricted left and right ranges that slider i can move
- $q_i^{mix}$ is the current position of slider i where $q_i^{left} \geq q_i^{max} \geq q_i^{mix} \geq q_i^{min} \geq q_i^{limit} \geq q_i^{right}$.

In a typical session, the user starts with a preferred plan, say $x_1$ corresponding to mixing vector $$\alpha = \begin{pmatrix} 1 \\ 0 \\ \vdots \\ 0 \end{pmatrix}.$$

Then, at each step, the user may take one of two actions: change the limit position $q_i^{limit}$ of any slider i or change the mixed position $q_i^{mix}$ of any slider i.

Changing the limit position of a slider does not affect the current positions $q^{mix}$ of any of the sliders but does change the restricted ranges ($q^{max}$, $q^{min}$) that they can move. The system calculates $q^{max}$, $q^{mmi}$ in real-time as the user changes the limit position $q_i^{limit}$ of any slider i.

Changing the mixed position $q_i^{mix}$ of a slider (by moving the slider left or right restricted by the ranges $q_i^{left} \geq q_i^{max} \geq q_i^{mix} \geq q_i^{min} \geq q_i^{limit} \geq q_i^{right}$) causes the system to generate a new mixing vector $\alpha$. By one approach the new mixing vector $\alpha$ must have non-negative elements that sum to 1, must satisfy $(Q \times \alpha)_i = q_i^{mix}$ for the currently moving slider i, and must satisfy the limit restrictions for all sliders $Q \times \alpha \geq q^{limit}$.

With these constraints, the mixing vector $\alpha$ is chosen to minimize the maximum rightward movement of the other N−1 "free" sliders. In the case that all other free sliders move left in response to the movement of slider i, the mixing vector $\alpha$ is chosen to maximize the minimum leftward movement of the free sliders. It is presumed that the new mixing vector $\alpha$ will result in a new solution $x^{mix}=X \times \alpha$ on the Pareto Surface of the plans in the plan database. If $x^{mix}$ is not on the Pareto Surface, a new $\alpha$ corresponding to a point on the Pareto Surface will be chosen. The concept of the Pareto Surface is well-known to those versed in the art of multi-criteria optimization.

In a typical workflow, the system displays an image of the PTV on which the structures of interest have been contoured. Given a treatment plan x, the system can calculate radiation dose to each point on these images and display the dose using conventional approaches such as isodose contours or as a dose color wash. The system can also display the dose to each structure as a dose-volume-histogram chart that has increasing dose values as its horizontal axis and the percentage of the structure with dose≥a given dose value as its vertical axis.

By way of example, a typical plan mixing workflow can be described as follows.

First, the user begins with a plan database represented by the pair (X, Q) and an initial $\alpha$. The absolute ranges $q^{left}$ and $q^{right}$ are set once from Q as described above. The restricted ranges are initialized to $q^{max}=q^{left}$ and $q^{min}=q^{limit}=q^{right}$, and the current slider positions are $q^{mix}=Q \times \alpha$. Next, the system calculates $x^{mix}=X \times \alpha$, calculates the radiation dose corresponding to $x^{mix}$ and displays that dose using conventional approaches as described above.

The system then displays all 6 quantities associated with each slider and waits for any responsive user input/interactions. If and when the user changes the limit position $q_i^{limit}$ of a slider, the system calculates new allowable ranges ($q^{max}$, $q^{min}$) for all sliders, then updates the display of all 6 quantities associated with each slider and awaits a next user interaction. If and when the user changes the mixed position $q_i^{mix}$ of a slider, the system calculates a new mixing vector $\alpha$ and new slider positions $q^{mix}=Q \times \alpha$, following which the system again calculates $x^{mix}=X \times \alpha$ and the radiation dose corresponding to $x^{mix}$ following which that resultant dose is displayed and the system continues as described above.

The present teachings supplement the foregoing by allowing new types of user input. In particular, and as one example, with a mouse the user can click down at some 3D point p on the PTV where the current dose is d and then, as the user drags the mouse to other points q on the PTV, the system calculates a new mixing vector $\alpha$ according to the above method with an additional constraint that the dose at 3D point q must be d. When the user releases the mouse at some point q, the system displays a spatial indicator to show that the dose at q is locked to d. So long as the spatial dose lock indicator is in place, the dose at that indicator will be locked to its current value. Furthermore, the system allows more than one such indicator to be simultaneously present. The spatial restrictions on dose limit the values that a can take and change the ranges $q^{max}$, $q^{min}$ for all sliders. After adding a spatial dose lock, and calculating an α corresponding to the lock, the system proceeds from the above-described step of calculating $x^{mix}=X \times \alpha$, calculating the radiation dose corresponding to $x^{ix}$, and displaying that dose.

In addition, and again with a mouse, the user can navigate to a previous spatial dose lock and move the lock to a new position or delete the lock. After moving or deleting a spatial dose lock, and calculating an α corresponding to that action, the system can then again proceed from the above-described step of calculating $x^{mix}=X \times \alpha$, calculating the radiation dose corresponding to $x^{mix}$, and displaying that dose.

As noted previously, these teachings are highly flexible and will accommodate various modifications and/or supplemental inclusions. By one approach, for example, the user clicks down at some 3D point where the dose has some value, say g Gy. Then as they drag the mouse to other points p, the mixed plan changes so that the dose under the present cursor position (displayed as isodose contours or dose color wash) at p becomes g Gy. If desired, after the user releases the mouse at some point p, they could subsequently set a range for the dose value at that point, say $g_{min} \leq g \leq g_{max}$. This would serve to allow some variation in the dose at that position. If the user subsequently moves a slider or drags a dose at some other 3D position, the dose at p would be allowed to vary to any value between $g_{min}$ and $g_{max}$.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method to facilitate shaping a radiation treatment dose comprising:
   by a control circuit:
      accessing a plurality of at least three different radiation treatment plans for a particular patient;
      forming a mixed radiation treatment plan from the at least three different radiation treatment plans;
      presenting on a display a plurality of dose volume histograms for the mixed radiation treatment plan, wherein at least one of the dose volume histograms depicts a first histogram that relates radiation dose to a target volume and another of the dose volume histograms depicts a second histogram that relates radiation dose to an organ at risk;
      presenting on the display an overlay of calculated radiation dose from the mixed radiation treatment plan on a treatment planning image volume;
      detecting a user's manipulation of one of the dose volume histograms, and in response thereto, modifying on the display at least one other of the dose volume histograms as a function of a mix of at least two of the plurality of different radiation treatment plans;
      detecting a user's real-time manipulation of the overlay of the calculated radiation dose and in response thereto modifying on the display in real-time the plurality of dose volume histograms and the overlay of the calculated radiation dose.

2. The method of claim 1 wherein the plurality of different radiation treatment plans comprises a plurality of different multi-criteria optimization radiation treatment plans.

3. The method of claim 2 wherein each of the multi-criteria optimization radiation treatment plans includes a representative multi-dimensional vector.

4. The method of claim 3 wherein the control circuit is configured to modify on the display the at least one other of the dose volume histograms as a function of a mix of at least two of the plurality of different radiation treatment plans by varying a weighting factor as corresponds to the representative multi-dimensional vector for mixed radiation treatment plans.

5. The method of claim 1 wherein the plurality of different radiation treatment plans all presume the administration of radiation to the particular patient via brachytherapy.

6. The method of claim 1 wherein the plurality of different radiation treatment plans all presume the administration of radiation to the particular patient via an external radiation beam.

7. The method of claim 1 further comprising:
   also presenting on the display, simultaneously with presenting the plurality of dose volume histograms, a plurality of user-interactive indicators that collectively represent dosing trade-offs amongst a plurality of patient volumes.

8. The method of claim 7 wherein the plurality of user-interactive indicators comprise sliders.

9. The method of claim 7 wherein the control circuit is further configured to modify the display of the dose volume histograms in response to a user's manipulation of one of the plurality of user-interactive indicators.

10. The method of claim 1 wherein presenting on the display an overlay of the calculated radiation dose from the mixed radiation treatment plan on the treatment planning image volume comprises displaying at least one of:
    a set of isodose contours;
    dose color washes.

11. An apparatus to facilitate shaping a radiation treatment dose comprising:
    a control circuit configured to:
       access a plurality of at least three different radiation treatment plans for a particular patient;
       form a mixed radiation treatment plan from the at least three different radiation treatment plans;
       present on a display a plurality of dose volume histograms for the mixed radiation treatment plan, wherein at least one of the dose volume histograms depicts a first histogram that relates radiation dose to a target volume and another of the dose volume histograms depicts a second histogram that relates radiation dose to an organ at risk;
       present on the display an overlay of calculated radiation dose from the mixed radiation treatment plan on a treatment planning image volume;
       detect a user's manipulation of one of the dose volume histograms, and in response thereto, modifying on the display at least one other of the dose volume histograms as a function of a mix of at least two of the plurality of different radiation treatment plans;
       detect a user's real-time manipulation of the overlay of the calculated radiation dose and in response thereto modifying on the display in real-time the plurality of dose volume histograms and the overlay of the calculated radiation dose.

12. The apparatus of claim 11 wherein the plurality of different radiation treatment plans comprises a plurality of different multi-criteria optimization radiation treatment plans.

13. The apparatus of claim 12 wherein each of the multi-criteria optimization radiation treatment plans includes a representative multi-dimensional vector.

14. The apparatus of claim 13 wherein the control circuit is further configured to modify on the display the at least one other of the dose volume histograms as a function of a mix of at least two of the plurality of different radiation treatment plans by varying a weighting factor as corresponds to the representative multi-dimensional vector for mixed radiation treatment plans.

15. The apparatus of claim 12 wherein the control circuit is configured to present on the display the overlay of the calculated radiation dose from the mixed radiation treatment plan on the treatment planning image volume by displaying at least one of:
 a set of isodose contours;
 dose color washes.

16. The apparatus of claim 11 wherein the plurality of different radiation treatment plans all presume the administration of radiation to the particular patient via brachytherapy.

17. The apparatus of claim 11 wherein the plurality of different radiation treatment plans all presume the administration of radiation to the particular patient via an external radiation beam.

18. The apparatus of claim 11 wherein the control circuit is further configured to:
 also present on the display, simultaneously with presenting the plurality of dose volume histograms, a plurality of user-interactive indicators that collectively represent dosing trade-offs amongst a plurality of patient volumes.

19. The apparatus of claim 18 wherein the plurality of user-interactive indicators comprise sliders.

20. The apparatus of claim 18 wherein the control circuit is further configured to modify the display of the dose volume histograms in response to a user's manipulation of one of the plurality of user-interactive indicators.

* * * * *